(12) United States Patent
Stearns

(10) Patent No.: US 8,529,516 B2
(45) Date of Patent: Sep. 10, 2013

(54) SYRINGE FOR INJECTION THROUGH ZONE OF BODY

(75) Inventor: Stanley D. Stearns, Houston, TX (US)

(73) Assignee: Gabriel Institute, Inc., Houston, TX (US)

( * ) Notice: Subject to any disclaimer, the term of this patent is extended or adjusted under 35 U.S.C. 154(b) by 0 days.

(21) Appl. No.: 12/276,637

(22) Filed: Nov. 24, 2008

(65) Prior Publication Data

US 2010/0004604 A1    Jan. 7, 2010

Related U.S. Application Data

(60) Provisional application No. 61/078,674, filed on Jul. 7, 2008.

(51) Int. Cl.
*A61M 5/00* (2006.01)

(52) U.S. Cl.
USPC ........... 604/187; 604/195; 604/196; 604/198; 604/110; 604/125

(58) Field of Classification Search
USPC .................. 604/192–198, 110, 187, 125
See application file for complete search history.

(56) References Cited

U.S. PATENT DOCUMENTS

| | | | |
|---|---|---|---|
| 984,037 A * | 2/1911 | Sheets | 604/125 |
| 4,392,859 A | 7/1983 | Dent | |
| 5,125,414 A * | 6/1992 | Dysarz | 600/576 |
| 5,514,100 A | 5/1996 | Mahurkar | |
| 5,891,105 A * | 4/1999 | Mahurkar | 604/195 |
| 6,056,716 A | 5/2000 | D'Antonio et al. | |
| 2004/0050864 A1 | 3/2004 | Stradella | |
| 2010/0049140 A1 | 2/2010 | Marsh et al. | |
| 2010/0185152 A1 | 7/2010 | Larsen et al. | |
| 2011/0238009 A1 | 9/2011 | Meron et al. | |

OTHER PUBLICATIONS

Webster's II New College Dictionary (1995), Boston, MA: Houghton Mifflin Company, pp. 19 and 72.*
Sholl, Linda, Notification of Transmittal of International Preliminary Report on Patentability—PCT/US09/49669, Jul. 27, 2010, 1 page, United States Patent and Trademark Office as Examining Authority, Alexandria, Virginia USA.

(Continued)

*Primary Examiner* — Kevin C Sirmons
*Assistant Examiner* — Edelmira Bosques
(74) *Attorney, Agent, or Firm* — James E. Hudson, III; Crain, Caton & James, P.C.

(57) ABSTRACT

A syringe which disperses medicate across a zone in the body during apparent conventional operation. The improved syringe includes a barrel, a plunger, and an operating cylinder. In operation, the needle of the syringe is inserted into the body at the distal portion of the portion of the body which is to receive the medicate. A single arm is attached to the barrel and passes through an operating cylinder with a thumb rest on its top. As a result, in operation, the user draws the single arm up to the thumb rest, thus causing the syringe to withdraw during injection and leaving a patch of medicate during operation.

3 Claims, 3 Drawing Sheets

(56) References Cited

OTHER PUBLICATIONS

Sholl, Linda, International Preliminary Report on Patentability—PCT/US09/49669, Jul. 27, 2010, 6 pages, United States Patent and Trademark Office as Examining Authority, Alexandria, Virginia USA.

Blaine R. Copenheaver, Notification of Transmittal of the International Search Report and the Written Opinion of the International Searching Authority, or the Declaration; International Application No. PCT/US2012/060818; Jan. 2, 2013, 1 page, International Searching Authority, Alexandria, Virginia, US.

Blaine R. Copenheaver, International Search Report, International Application No. PCT/US2012/060818; Jan. 2, 2013, 2 pages, International Searching Authority, Alexandria, Virginia, US.

Blaine R. Copenheaver, Written Opinion of the International Searching Authority, International Application No. PCT/US2012/060818; Jan. 2, 2013, 4 pages, International Searching Authority, Alexandria, Virginia, US.

Reiko Tanaka, Notice of Reasons for Rejection—Japanese Patent Application No. 2011-517497, Jun. 25, 2013, 2 pages, Japan Patent Office, Tokyo, Japan.

* cited by examiner

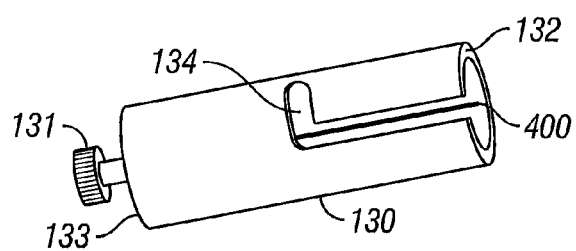
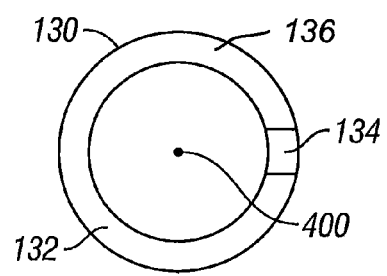
FIG. 4          FIG. 5
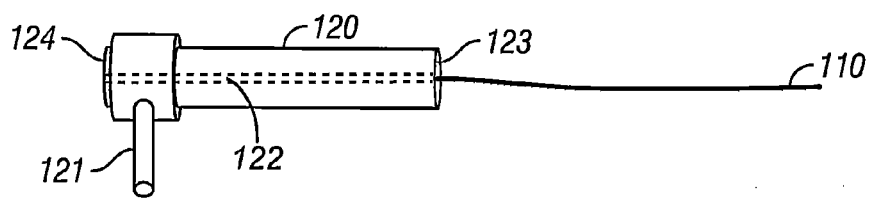
FIG. 6
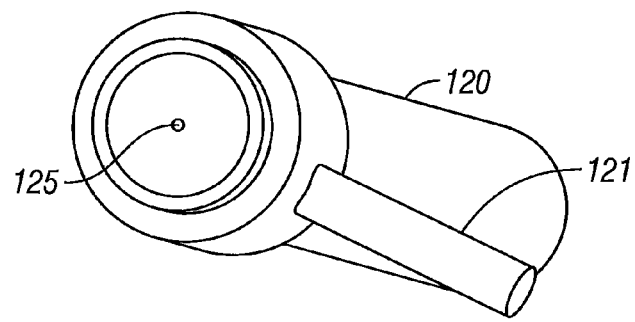
FIG. 7

SYRINGE FOR INJECTION THROUGH ZONE OF BODY

CROSS REFERENCE TO RELATED APPLICATIONS

This application claims the benefit of U.S. Provisional Patent Application No. 61/078,674 entitled, "Syringe for injection through zone of body" filed on Jul. 7, 2008 in the United States Patent and Trademark Office.

STATEMENT REGARDING FEDERALLY SPONSORED RESEARCH OR DEVELOPMENT

Not Applicable.

BACKGROUND OF THE INVENTION

1. Field of the Invention

The present invention relates to an apparatus for delivery of medical treatment through a zone of a body. More particularly, the invention relates to devices and systems for the delivery and injection of therapeutic agents, solutions or injectates throughtout a portion of bodily tissue. Additionally, the invention relates to methods of delivering and injecting a solution across a target site within the body for the treatment of that target site.

2. Description of the Related Art

Hypodermic syringes are widely used in the medical field for administering medicaments. Generally, hypodermic syringes include a needle having a sharpened distal point for penetrating vial stoppers or patient's body. The needle is attached either fixedly or removably to a syringe barrel. In operation, these syringes provide the means to deliver medicaments to a single specific location in the body. In operation, the plunger is depressed into the barrel and the medicament thus discharged. This system, largely unchanged since the invention of the syringe, contemplates delivery of the therapeutic agent at a single location wherein the effect of the therapeutic agent is transmitted through adjacent cells. Problematically, when the therapeutic agent is intended to act against a collection of cells, its effectiveness is reduced and/or delayed by such transmission, even though the overall distance from one side of the collection of cells to the other may be quite small. Practitioners have attempted to overcome this limitation and provide the benefit of a dispersed delivery by simultaneously depressing the syringe plunger with the thumb while also withdrawing the syringe. However, this technique is difficult to learn and is ineffective to properly deliver the therapeutic agent to the desired location in the desired quantities, particularly when the desired location has defined boundaries, such as a tumor.

There is therefore a need for a syringe that disburses a therapeutic agent along a collection of cells in a body.

SUMMARY OF THE INVENTION

It is therefore, a principle object of the present invention to provide a syringe which disburses a therapeutic agent along a collection of cells in a body from a single action by the operator.

The foregoing advantages are achieved through a new syringe having a barrel, a plunger, and an operating cylinder encapsulating the barrel and retaining within its body the plunger. Unlike convention syringes where the barrel of the syringe includes a flange at its first end, the barrel of the present syringe includes a single arm, preferably at its first end, positioned generally perpendicular to the barrel. The operating cylinder includes a passage from its second end towards its first end which permits movement of the single arm from a position at the operating cylinders second end to a point near its first end. At its first end, the operating cylinder provides a thumb rest. Centered within the operating cylinder proximate its first end is the plunger of the syringe. Thus, in operation, the needle of the syringe is inserted into the body at the distal portion of the portion of the body to receive the therapeutic agent and the single arm of the syringe drawn toward the thumb rest of the operating cylinder. This natural movement, generated by the thumb outstretched as a backing and the index finger drawing the arm toward the thumb, provides dispersion of the medicant along the needle's path while simultaneously withdrawing the needle.

The foregoing and other objectives, features and advantages of the invention will be more readily understood upon consideration of the following detailed description of the invention, taken in conjunction with the accompanying drawings.

BRIEF DESCRIPTION OF THE DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only a typical preferred embodiment of the invention and are therefore not to be considered limiting of its scope as the invention may admit to other equally effective embodiments.

FIG. 4 illustrates the operating cylinder of the present invention and the plunger therein.

FIG. 5 illustrates another view of the operating cylinder of the present invention and the plunger therein.

FIG. 6 illustrates a view of the barrel of the present invention with needle attached.

FIG. 7 illustrates another view of the barrel of the present invention.

DETAILED DESCRIPTION OF THE PREFERRED EMBODIMENT

The present invention involves an improvement of delivery of an injection through a zone of a body. More particularly, the invention involves a syringe for the delivery and injection of therapeutic agents, solutions or injectates over a portion of bodily tissue rather than in a single location, which apparently functioning as a conventional syringe.

Figure 1:
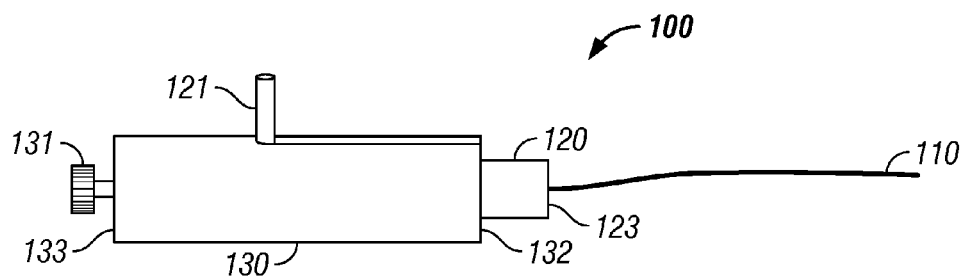
FIG. 1 illustrates the syringe of the present system in its contracted position.
Figure 2:
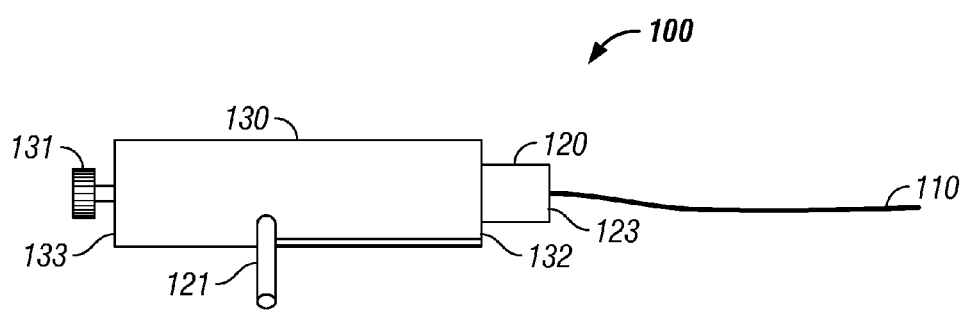
FIG. 2 illustrates another view of the syringe of the present system in its contracted position.

Referring to FIGS. 1 and 2, in a preferred embodiment the invention 100 includes a barrel 120, and an operating cylinder 130. In operation, a needle 110 is affixed to the barrel 120. Needle 110 may be permanently affixed to barrel 120 or may be replaceable and affixed only during use. The barrel 120 includes a barrel single arm 121. The barrel 120 is at least partially positioned with the operating cylinder 130, which has an operating cylinder wall 136 defining an inner diameter nearly equivalent to the outer diameter of the barrel 120 but with sufficient allowance to permit the barrel 120 to slide easily within operating cylinder 130. When the invention 100 is fully contracted, as illustrated in FIGS. 1 and 2, the barrel 120 is almost entirely within operating cylinder 130. Operating cylinder 130 includes at its first end 133 a thumb rest 131 that provides a natural location for a user to position a thumb.

Figure 3:
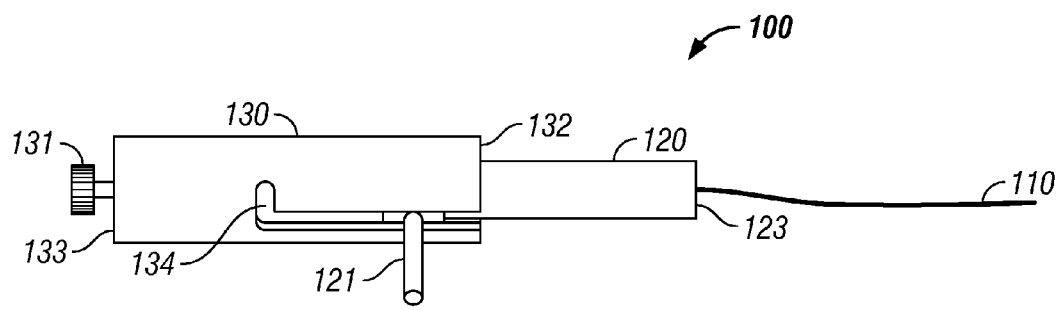
FIG. 3 illustrates the syringe of the present system in its extended position.

Referring to FIG. 3, depicting the invention 100 in the extended position, barrel single arm 121 is passes through operating cylinder arm passage 134 near operating cylinder second end 132, thus positioning barrel 120 at the point most distant from the operable end of plunger 400 (not shown). During the repositioning of the barrel 120 from the contracted to the extended position, needle 110 is typically in communication with the medicate, thus drawing the desired volume of medicate into the needle 110 and the barrel 120. The vacuum created by this repositioning of the barrel 120 and the drawing of medicate into the syringe barrel 120 is consistent with standard syringe operation.

Referring to FIGS. 4 and 5, unlike conventional syringes where the plunger 400 extends outside the syringe body and is drawn backwards to create a vacuum to draw the medicate into the barrel 120, plunger 400 of the present invention is integrally affixed internal the operating cylinder 130 near the operating cylinder first end 133, and fixed in relative position to the operating cylinder 130. Thus, the movement of the operating cylinder 130 is consistent with the movement of plunger 400 into barrel 120. The plunger 400 thus moves only simultaneously in the same direction with the operating cylinder 130 relative to the barrel 120.

Turning to FIGS. 6 and 7, the barrel 120 of the present invention is further illustrated. The barrel 120 includes a first end 124 and a second end 123. The needle 110 communicates with the barrel 120 at its second end 123. The plunger 400 enters internal passage 122 of the barrel 120 at the barrel's first end 124. Also, at or near barrel first end 124, barrel single arm 121 is affixed. Communication between barrel 120 and operating cylinder 130 is provided at barrel plunger opening 125, located adjacent the barrel first end 124.

The single sided positioning of the barrel single arm 121 on barrel 120, its extension beyond operating cylinder 130 and the thumb rest 131 of operating cylinder cause operation of the syringe invention 100 to accomplish its intended goal—delivering and injecting a solution along a target site within the body for the treatment of that target site. Traditional syringes which include a ring, dual loop, or other extension at the second end of the barrel, causing operation by the user grasping the barrel of syringe on two sides and causing depression of the plunger by driving the opposing thumb into the barrel. The present invention accomplishes the opposite action. Because the present invention includes a single-sided arm, the user positions one finger about the barrel single arm 121, like a trigger, and the outstretched thumb at the thumb rest 131 at the operating cylinder first end 133. The user then maintains the thumb and arm in position while pulling the barrel single arm 121 like a trigger, i.e. toward the thumb rest 131. As a result, the barrel 120 is driven rearward into plunger 400 within operating cylinder 130. The medicate within barrel 120 is thus driven into needle 110 while needle 110, along with barrel 120 is being repositioned toward the operating cylinder first end 133 and the thumb rest 131. The medicate therefore is ejected while the needle 110 is being withdrawn.

The present invention provides significant advantages over the prior art. When high ph radioisotopes are used in treating illness, it is undesirable for the radioisotope to mix with the blood. Rather, it is desirable to deposit the radioisotope along a line in the tissue, particularly along the path of needle 100 through the body tissue. It appears the high ph radioisotope typically reacts with the tissue, causing coagulation of the microcapillaries and precluding entry of the radioisotope into the bloodstream. Injection of the total volume of the liquid, however, does cause undesirable loss of the radioisotope into the bloodsteam. Ideally, a plurality of injection lines are utilized, as the range of the radioisotope is quite small, often in the range of six (6) millimeters (mm) on each side of the injection line. A plurality of injection lines, each corresponding to the needle path, therefore, blankets the tumor, with a substantial portion, potentially nearing ninety percent (90%) of the radioisotope remaining in the tumor and being effective there, with only a de minimus portion entering the remainder of the body, in quantities sufficiently low to pose a substantially lower risk of injury that current methods.

The system provides a further benefit is zero pressure differential as the bore of the syringe is equal to or less than the diameter of the needle.

As can be appreciated, the intended operation may be encouraged by providing a surface for thumb rest 131, which discourages the user from applying pressure directly to it.

Figure 8:
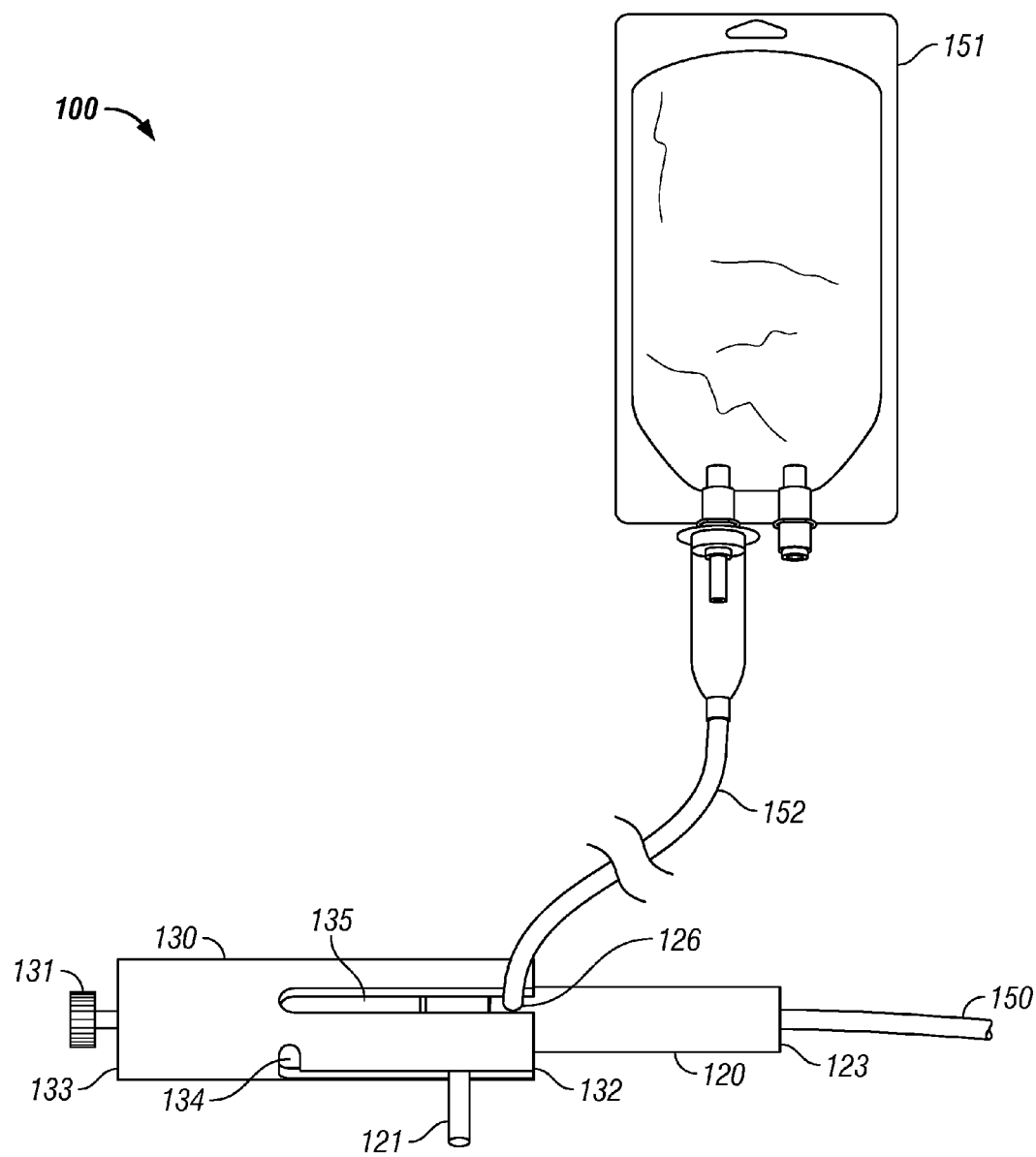
FIG. 8 illustrates an alternative embodiment of the present invention for use with an external fluid supply.

In an alternative embodiment, illustrated in FIG. 8, this operation may be utilized to introduce a liquid through a catheter 150, rather than a needle 110, while simultaneously withdrawing the catheter 150. Such use requires that the barrel 120 have an external fluid orifice 126 to provide fluid communication via a piping 152, which may be IV tubing, with an external fluid supply 151 which otherwise provides fluid flow to the catheter 150. This may be accomplished by communication of the external fluid supply 151 to barrel 120, preferably by a connection passing through a liquid supply passage 135 wherein liquid supply passage 135 is aligned with external fluid orifice 125.

Various alternatives and/or modifications may be made to the disclosed embodiments without departing from the spirit or scope of the invention.

I claim:

1. A syringe comprising
an operating cylinder,
a barrel, having a barrel first end and a barrel second end, a barrel arm attached to said barrel and extending outward from said barrel, said barrel sized to slide within said operating cylinder, said barrel having an internal passage therethrough;
said operating cylinder having an operating cylinder first end, an operating cylinder second end, an operating cylinder wall, a thumb rest proximate to said operating cylinder first end and an operating cylinder arm passage through said operating cylinder wall sized to said barrel arm, said operating cylinder arm passage extending from said operating cylinder second end towards said operating cylinder first end, said barrel arm passing through said operating cylinder wall at said operating cylinder arm passage; and
a plunger internally integrally affixed to said operating cylinder proximate to said operating cylinder first end and fixed in relative position to said operating cylinder to move only simultaneously in the same direction with said operating cylinder relative to said barrel, sized to enter said internal passage of said barrel at said barrel first end.

2. The syringe of claim 1 further comprising:
a needle affixed to said barrel proximate to said barrel second end.

3. The syringe of claim 1 further comprising:
said barrel having an external fluid orifice;
an external fluid supply communicating with said barrel via a piping communicating to said external fluid orifice; and
said operating cylinder having a liquid supply passage sized to said piping.

\* \* \* \* \*